United States Patent [19]

Sugimoto et al.

[11] Patent Number: 4,789,669

[45] Date of Patent: Dec. 6, 1988

[54] VAGINAL SUPPOSITORY

[75] Inventors: Isao Sugimoto, Nara; Hiroyuki Tsuta, Nakaniikawa, both of Japan

[73] Assignee: Kanebo, Ltd., Tokyo, Japan

[21] Appl. No.: 24,204

[22] Filed: Mar. 10, 1987

[30] Foreign Application Priority Data

Oct. 20, 1986 [JP] Japan .................................. 61-250157

[51] Int. Cl.$^4$ .............................................. A61K 31/56
[52] U.S. Cl. .................... 514/178; 514/967; 514/935
[58] Field of Search ............................... 514/178, 967

[56] References Cited

U.S. PATENT DOCUMENTS 4,005,200 1/1977 Utsumi et al. ...................... 514/178
4,061,744 12/1977 Sugimoto et al. ................. 260/397.4
4,496,556 1/1985 Orentreich ........................... 514/178

FOREIGN PATENT DOCUMENTS 2126086 3/1984 United Kingdom ............... 514/967

Primary Examiner—Leonard Schenkman
Assistant Examiner—Joseph A. Lipovsky
Attorney, Agent, or Firm—Millen & White

[57] ABSTRACT

A vaginal suppository comprising a pharmaceutically acceptable salt of dehydroepiandrosterone sulfate and a hard fat with a hydroxyl value not exceeding 50. This vaginal suppository is useful for improving the ante-partum condition of pregnant women and features an extended shelf life.

8 Claims, No Drawings

VAGINAL SUPPOSITORY

BACKGROUND OF THE INVENTION

1. Field of the Invention

The present invention relates to vaginal suppositories. More particularly, this invention relates to a vaginal suppository comprising a pharmaceutically acceptable salt of dehydroepiandrosterone sulfate (DHAS) and a hard fat with a hydroxyl value not exceeding 50.

2. Description of the Prior Art

Pharmaceutically acceptable salts of DHAS promote maturation of the uterine cervix at late pregnancy and enhance the responsiveness of uterine smooth muscle to oxytocin and clinically injections containing its sodium salt have been used as drugs of choice in ante-partum indications in Japan (U.S. Pat. Nos. 4,005,200 and 4,061,744).

The object of the present invention is to provide a vaginal suppository which is suitable for administration by the intravaginal route, which is relatively expedient, and which has a long shelf life.

The inventor's exploratory evaluation of various lipophilic bases and hydrophilic bases for possible use as the base in vaginal suppositories containing a pharmaceutically acceptable salt of DHAS has shown that a vaginal suppository manufactured by using a hard fat having a hydroxyl value not exceeding 50 has a long shelf life and produces a marked improvement in the ante-partum condition of pregnant women. The present invention is predicated on the above finding.

SUMMARY OF THE INVENTION

This invention relates to a storagestable vaginal suppository comprising pharmaceutically acceptable salt of dehydroepiandrosterone sulfate inadmixture with a hydrophobic baseconsisting essentially of 1 to 20 parts by weight of said salt of a hard fat with a hydroxyl value not exceeding 50.

DETAILED DESCRIPTION

The term "hard fat" as used herein means a mixture of the monoglyceride, diglyceride and triglyceride of straight-chain saturated fatty acids containing 8 to 18 carbon atoms and examples of such mixture are mentioned in the literature, e.g. Martindale The Extra Pharmacopoeia 28th edition, edited by James E. F. Reynolds, Page 1067, The Pharmaceutical Press, London, 1982 and Standards for Ingredients of Drugs not in the Japanese Pharmacopeia (Edited by Pharmaceutical Affairs Bureau, Ministry of Health and Welfare in Japan, page 1239, Oct. 1, 1986, Yakugyo Jiho Co., Ltd. Tokyo, Japan). In the present invention, such a hard fat having a hydroxyl value not more than 50 is employed. The hard fats having a hydroxyl value not more than 50 are commercially available, for example under the trade marks Witepsol H-35, H-5, H-15 and W-35 by Dynamit Nobel Co. and Nissan Pharmasol B-115 by Nippon Oil & Fats Co., Ltd. Any vaginal suppository manufactured using a hard fat with a hydroxyl value in excess of 50 shows a poor shelf life, tends to become colored during storage and transit, and suffers from a degradation of the pharmaceutically acceptable salt of DHAS mainly into DHA.

As examples of said pharmaceutically acceptable salt of DHAS, there may be mentioned various metal salts of DHAS such as the sodium salt, potassium salt, lithium salt, magnesium salt, etc. and the ammonium salt.

The vaginal suppository according to the present invention can be manufactured by the following method, for instance. A hard fat with a hydroxyl value not exceeding 50 is melted by heating and a pharmaceutically acceptable salt of DHAS is evenly mixed with the melt. The mixture is cast into molds in predetermined quantities and cooled to give vaginal suppositories of the present invention.

The pharmaceutically acceptable salt of DHAS is preferably in the form of a crystalline powder whose average particle diameter is 3 to 20 $\mu$m. If the average particle diameter exceeds 20 $\mu$m, the salt of DHAS cannot be easily dispersed uniformly in the hard fat so that a variation in DHAS content tends to occur among individual suppositories as well as within each suppository.

The ratio of said hard fat to said pharmaceutically acceptable salt of DHAS is generally 1 to 20 weight parts, to each weight part of the salt.

The vaginal suppository according to the present invention is administered to pregnant women at the 37th to 39th week of gestation usually in a dose of 100 to 1500 mg as the pharmaceutically acceptable salt of DHAS with a frequency of once to 3 times a day.

The vaginal suppository according to the present invention has a satisfactory shelf life. When a vaginal suppository manufactured using a hydrophilic base or one manufactured using a hard fat with a hydroxyl value exceeding 50 is stored at a temperature of 35° C., the pharmaceutically acceptable salt of DHAS contained therein is partly decomposed to give DHA and, at the same time, the suppository becomes colored. In contrast, the vaginal suppository according to the present invention does not undergo decomposition, nor is it colored, under the comparable conditions as will be seen from Test Example 1 given hereinafter.

Furthermore, the vaginal suppository according to the present invention remarkably accelerates the maturation of the uterine cervix (Test Example 2) and is low in toxicity (Test Example 3). Therefore, the vaginal suppository according to the present invention is useful for improving the ante-partum condition of pregnant women.

The following test examples are intended to illustrate the usefulness of the vaginal suppository according to the present invention.

TEST EXAMPLE 1

Shelf-life test

1. Samples

Six vaginal suppositories according to the present invention, each containing sodium DHAS dihydrate, and five different control suppositories were used as samples. The weight ratio of the base to sodium DHAS dihydrate in each sample was 1:9 except that it was 2:8 in the vaginal suppository of Example 6.

Vaginal suppository of Example 1 (base: a hard fat with a hydroxyl value of 2.3)

Vaginal suppository of Example 2 (base: a hard fat with a hydroxyl value of 3.0)

Vaginal suppository of Example 3 (base: a hard fat with a hydroxyl value of 11.6)

Vaginal suppository of Example 4 (base: a hard fat with a hydroxyl value of 12.3)

Vaginal suppository of Example 5 (base: a hard fat with a hydroxyl value of 46.0)

Vaginal suppository of Example 6 (base: a hard fat with a hydroxyl value of 11.6)
Vaginal suppository of Control Example 1 (base: a hard fat with a hydroxyl value of 53.5)
Vaginal suppository of Control Example 2 (base: a hard fat with a hydroxyl value of 54.3)
Vaginal suppository of Control Example 3 (base: a hard fat with a hydroxyl value of 64.1)
Vaginal suppository of Control Example 4 (base: a hydrophilic base =a 4:5 (w/w) mixture of Macrogol 4000 and Macrogol 1540)
Vaginal suppository of Control Example 5 (base: a hydrophilic base =polyoxyethylene-polyoxypropylene glycol)

2. Method

Ten specimens of each test suppository immediately after manufacture were stored in an incubator at 35° C. and after 2 and 6 months of storage, each specimen was examined for appearance and for the decomposition product (DHA) of DHAS sodium salt. Detection of the decomposition product was performed by thin layer chromatography. Three specimens of each vaginal suppository were taken at random and after addition of 60 ml of methanol, they were combined and warmed at about 50° C. with vigorous stirring and allowed to cool in a water bath for 30 minutes. After centrifugation, the supernatant was taken and 10 $\mu$l portions were spotted on a silica gel plate (Kiesel gel 60 F 254, 0.25 mm thick, Merck). The chromatogram was developed over a distance of about 10 cm with a solvent mixture of chloroform, methanol and water (75:22:3, v/v). After the plate was dried in the air, it was uniformly sprayed with a 1:1 (v/v) mixture of concentrated sulfuric acid and ethanol and heated at 80° C. for 5 minutes. The DHAS sodium salt and its decomposition product were detected as colored spots. Under the above conditions, DHAS sodium salt gave a red-purple spot at Rf about 0.2 and the decomposition product DHA gave a pink spot at Rf about 0.73.

3. Results

The results of the above test are shown in Table 1.

nor did it give a decomposition product, even after prolonged storage.

On the other hand, the vaginal suppositories manufactured by using hard fats with hydroxyl values exceeding 50 suffered from coloration on storage. Moreover, the analysis of these suppositories by thin-layer chromatography revealed a pink spot at Rf about 0.73 and this decomposition product was identified to be DHA.

TEST EXAMPLE 2

Test on the extensibility of the uterine cervix

1. Sample

The vaginal suppository according to the present invention (a vaginal suppository of the same composition as Example 6; provided that it was prepared in the form of a cylinder with a diameter of 4 mm).

2. Test animals

Primiparous female Wistar rats (aged 13 weeks, 6 animals per group)

3. Method

Beginning on the 12th day of gestation, each sample suppository was intravaginally administered to rats in an amount of 100 mg once a day for 5 consecutive days. Control rats received the same base as used in the test drug (Witepsol ® H-15, Dynamit Nobel Co.) in a dose of 100 mg once a day. On the 17th day of gestation, the rats were sacrificed by decapitation and the uterine cervix was isolated. The uterine cervix was dissected at a site 3 mm apart from the point of connection of the cervix and formix viginae and using this uterine cervix specimen, the extensibility of uterine cervix was determined. Thus, one steel rod was inserted in parallel into each of the two cervical cannals of the isolated uterine cervix and one of the steel rods was pulled at a predetermined rate and the extension of the uterine cervix due to a change in tension acting on the cervix was recorded on an inkwriting oscillograph (Nihon Kohden Co., Ltd.) through a force displacement transducer (Nihon Kohden Co., Ltd.) connected to the other steel rod, with the length of extension of the uterine cervix plot-

TABLE 1

| Sample of vaginal suppository | Suppository base | Shelf life Test | | | |
|---|---|---|---|---|---|
| | | 2 months | | 6 months | |
| | | Color | Decomposition product | Color | Decomposition product |
| Example 1 | Hard fat with OH value = 2.3 | White | None | White | None |
| Example 2 | Hard fat with OH value = 3.0 | White | None | White | None |
| Example 3 | Hard fat with OH value = 11.6 | White | None | White | None |
| Example 4 | Hard fat with OH value = 12.3 | White | None | White | None |
| Example 5 | Hard fat with OH value = 46.0 | White | None | White | None |
| Example 6* | Hard fat with OH value = 11.6 | White | None | White | None |
| Control Example 1 | Hard fat with OH value = 53.5 | Light yellow brown | Detected | Yellow brown | Detected |
| Control Example 2 | Hard fat with OH value = 54.3 | Light yellow brown | Detected | Yellow brown | Detected |
| Control Example 3 | Hard fat with OH value = 64.1 | Light yellow brown | Detected | Yellow brown | Detected |
| Control Example 4 | Macrogol 4000 and 1540 (4:5) | White | None | Yellow brown | Detected |
| Control Example 5 | Polyoxyethylene-polyoxypropylene | Yellow brown | Detected | Yellow brown | Detected |

*The ratio of DHAS sodium dihydrate to the base in this sample is 2:8, by weight; the ratio in all other samples is 1:9.

Thus, the vaginal suppository manufactured by using a hard fat with a hydroxyl value not exceeding 50 according to the present invention showed no coloration, ted on the abscissa against the tension on the ordinate.

4. Result

Table 2 shows the lengths of extension which the cervix showed from the time when a tension of 5 g was applied to the time of application of a tension of 25 g.

TABLE 2

| | Length of extension (mm) Mean ± S.E. |
|---|---|
| Group treated with the vaginal suppository of the invention | 1.8 ± 0.29* |
| Control group | 1.0 ± 0.19 |

*$p < 0.05$ (t-test)

It is apparent that the vaginal suppository according to the present invention facilitates extension of the uterine servix. In other words, the vaginal suppository according to the present invention enhances the extensibility of the cervix and promotes its maturation.

TEST EXAMPLE 3

Acute toxicity test
1. Test drug

A hard fat with a hydroxyl value of 11.6 (Witepsol ® H-15, Dynamit Nobel Co.) was melted by heating and the same weight of sodium DHAS dihydrate (average particle diameter 7 μm) was added. After thorough mixing, the mixture was cooled in molds to give cylindrical suppositories 3 mm or 4 mm in diameter.

2. Test animals

Female SD rats (aged 6 weeks, 5 animals per group, body weights 149–168 g)

Female ICR mice (aged 6 weeks, 5 animals per group, body weights 24.7 to 27.1 g)

3. Method

Using the above suppositories, rats and mice with free access to food and water were intravaginally dosed with 500 mg/kg of sodium DHAS dihydrate. The suppositories with a diameter of 4 mm were administered to the rats and those with a diameter of 3 mm to the mice.

4. Results

The animals were observed for 14 days after administration but no death was found, nor was found a change in general condition.

The following examples and control examples are intended to illustrate the invention in further detail.

EXAMPLE 1

A stainless steel beaker was filled with 900 g of a hard fat with a hydroxyl value of 2.3 (Witepsol ® H-35, Dynamit Nobel Co.) and after melting at 40° to 42° C., 100 g of pulverized sodium DHAS dihydrate (average particle diameter: 7 μm) was added and evenly mixed. The mixture at 37°–38° C. was poured in 1 g portions into spindle-shaped molds and cooled to give vaginal suppositories each containing 100 mg of sodium DHAS dihydrate.

EXAMPLES 2 to 5

The procedure of Example 1 was repeated except that hard fats with hydroxyl values of 3.0, 11.6, 12.3 and 46.0 were used in lieu of the hard fat with a hydroxyl value of 2.3 to give vaginal suppositories each containing 100 mg of sodium DHAS dihydrate.

| | Hard fat |
|---|---|
| Example 2 | Witepsol ® H-5 (OH value = 3.0) (Dynamit Nobel Co.) |
| Example 3 | Witepsol ® H-15 (OH value = 11.6) (Dynamit Nobel Co.) |
| Example 4 | Nissan Pharmasol ® B-115 (OH value = 12.3) (Nippon Oil & Fats Co., Ltd.) |
| Example 5 | Witepsol ® W-35 (OH value = 46.0) (Dynamit Nobel Co.) |

EXAMPLE 6

In the same manner as Example 1, 800 g of a hard fat with a hydroxyl value of 11.6 (Witepsol ® H-15; Dynamit Nobel Co.) and 200 g of sodium DHAS dihydrate (average particle diameter 5 μm) were evenly mixed and 1 g portions of the mixture were filled into molds and cooled to give vaginal suppositories each containing 200 mg of sodium DHAS dihydrate.

Control Examples 1 to 3

The procedure of Example 1 wa repeated except that a hard fat with a hydroxyl value of 53.5, 54.3 or 64.1 was used in lieu of the hard fat with a hydroxyl value of 2.3 to give vaginal suppositories each containing 100 mg of DHAS sodium dihydrate.

| | Hard fat |
|---|---|
| Control Example 1 | Witepsol ® S-55 (OH value = 53.5) (Dynamit Nobel Co.) |
| Control Example 2 | Nissan Pharmasol ® T-115 (OH value = 54.3) (Nippon Oil & Fats Co., Ltd.) |
| Control Example 3 | Witepsol ® S-58 (OH value = 64.1) (Dynamit Nobel Co.) |

CONTROL EXAMPLE 4

A stainless steel beaker was charged with 400 g of Macrogol 4000 and 500 g of Macrogol 1540 and after melting at 55° to 60° C., 100 g of pulverized sodium DHAS dihydrate (average particle diameter 7 μm) was added and mixed. The mixture was filled in 1 g portions into spindle-shaped molds and cooled to give vaginal suppositories each containing 100 mg of sodium DHAS dihydrate.

CONTROL EXAMPLE 5

A stainless steel beaker was charged with 900 g of polyoxyethylene-polyoxypropylene glycol (Unilube ® 70DP-950B, Nippon Oil & Fats Co., Ltd.) and after melting at 55° to 60° C., 100 g of pulverized sodium DHAS dihydrate (average particle diameter 7 μm) was added and mixed. The mixture was filled in 1 g portions into spindle-shaped molds and cooled to give vaginal suppositories each containing 100 mg of sodium DHAS dihydrate.

We claim:

1. A storage stable vaginal suppository comprising a pharmaceutically acceptable salt of dehydroepiandrosterone sulfate in admixture with a hydrophobic base consisting essentially of 1 to 20 parts by weight of said salt of a hard fat with a hydroxyl value not exceeding 50.

2. The suppository of claim 1, wherein the pharmaceutically acceptable salt is the sodium dihydrate salt.

3. The suppository of claim 1, wherein the pharmaceutically acceptable salt is in the form of a crystalline powder whose average particle diameter is 3 to 20 μm.

4. The suppository of claim 1, wherein the suppository contains from 100 to 1500 mg of the pharmaceutically acceptable salt.

5. The suppository of claim 1, wherein the hard fat has a hydroxyl value of from 2.3 to 46.

6. The suppository of claim 1, wherein the weight ratio of the pharmaceutically acceptable salt to the hard fat is about 1:4 to 1:9.

7. The suppository of claim 1, wherein the pharmaceutically acceptacle salt is the sodium dihydrate salt; wherein the pharmaceutically acceptable salt is in the form of a crystalline powder whose average particle diameter is 3 to 20 μm; wherein the suppository contains from 100 to 1500 mg of the pharmaceutically acceptable salt; wherein the hard fat has a hydroxyl value of from 2.3 to 46; and wherein the weight ratio of the pharmaceutically acceptable salt to the hard fat is about 1:4 to 1:9.

8. In a method of administering a pharmaceutically acceptable salt of dehydroepiandrosterone sulfate to a pregnant woman to promote maturation of the uterine cervix during late pregnancy to enhance the responsiveness of the uterine mouth muscle to oxytocin, the improvement wherein the pharmaceutically acceptable salt is administered intravaginally at a dose of 100 to 1500 mg from one to 3 times daily, as a vaginal suppository according to claim 1.

* * * * *